United States Patent [19]

Knight et al.

[11] Patent Number: 5,266,209

[45] Date of Patent: Nov. 30, 1993

[54] METHOD AND APPARATUS FOR ANALYZING MATTER IN BIOLOGICAL FLUIDS USING LUMINESCENCE

[75] Inventors: Robert H. Knight; Janice H. Knight, both of Plymouth, United Kingdom

[73] Assignee: Knight Scientific Limited, United Kingdom

[21] Appl. No.: 801,781

[22] Filed: Dec. 6, 1991

[30] Foreign Application Priority Data

Dec. 6, 1990 [GB] United Kingdom ............... 9026538

[51] Int. Cl.⁵ ............................................. G01N 21/76
[52] U.S. Cl. ............................... 210/691; 210/498; 210/651; 250/459.1; 356/39; 422/52; 422/101; 436/172; 436/178; 436/905
[58] Field of Search ............... 210/651, 745, 767, 94, 210/299, 321.6, 483, 498, 541, 638, 690, 691, 650, 639, 634; 422/52, 101; 436/172, 178, 807, 905; 250/361 C, 458.1, 459.1, 461.2; 356/36, 39

[56] References Cited

U.S. PATENT DOCUMENTS

| | | | |
|---|---|---|---|
| 4,652,533 | 3/1987 | Jolley | 436/172 |
| 4,880,548 | 11/1989 | Pall et al. | 210/508 |
| 4,923,620 | 5/1990 | Pall | 210/767 |
| 4,925,572 | 5/1990 | Pall | 210/767 |
| 4,933,276 | 6/1990 | Baret | 422/52 |
| 4,948,975 | 8/1990 | Erwin et al. | 422/52 |
| 5,043,141 | 8/1991 | Wilson et al. | 422/52 |
| 5,057,431 | 10/1991 | Lubbers et al. | 436/172 |
| 5,096,809 | 3/1992 | Chen et al. | 436/178 |

FOREIGN PATENT DOCUMENTS

| | | |
|---|---|---|
| 0101398 | 2/1984 | European Pat. Off. . |
| 0335244 | 5/1990 | European Pat. Off. . |
| 2804117 | 8/1978 | Fed. Rep. of Germany . |
| 8807584 | 10/1988 | World Int. Prop. O. . |

OTHER PUBLICATIONS

Patent Abstracts of Japan, vol. 14, No. 232 (C-0719), May 17, 1990; & JP-A-2057197 (Japan Organo Co., Ltd.) Feb. 26, 1990.

*Primary Examiner*—Joseph W. Drodge
*Attorney, Agent, or Firm*—Larson & Taylor

[57] ABSTRACT

A method and apparatus is provided for analyzing the leucocytes in a biological fluid. The biological fluid is passed through a filter material having a critical wetting surface tension greater than 53 dynes/cm so that the leucocytes are held in the filter by adsorption. The filter material is subsequently treated with luminogenic material so that the treated filter may be analyzed by luminescence detection.

9 Claims, 2 Drawing Sheets

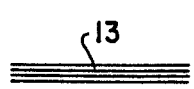
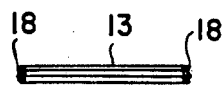
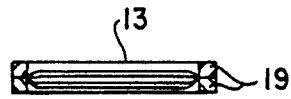
FIG.2(a)  FIG.2(b)  FIG.2(c)
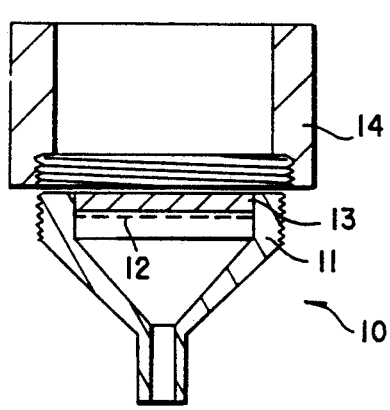
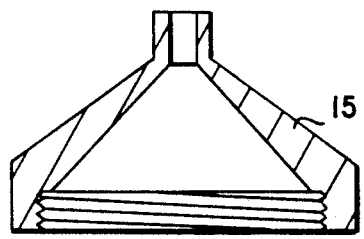
FIG.1(a)  FIG.1(b)
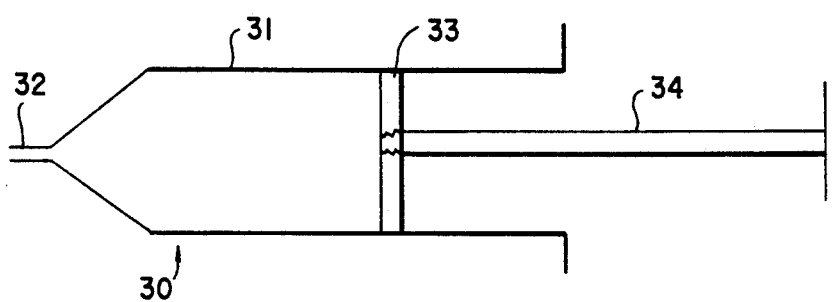
FIG.3(b)
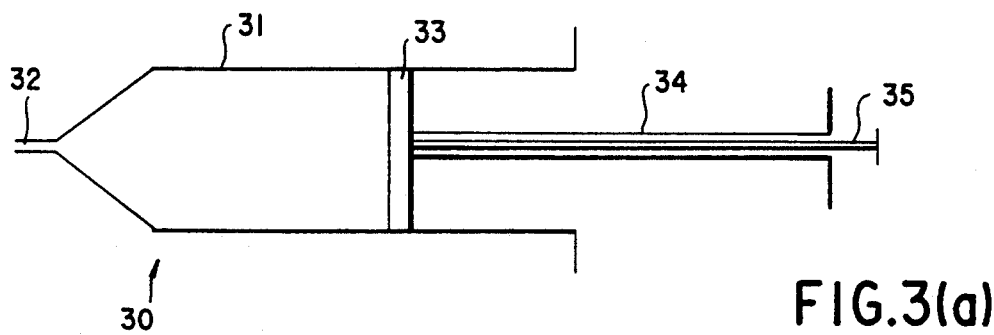
FIG.3(a)

METHOD AND APPARATUS FOR ANALYZING MATTER IN BIOLOGICAL FLUIDS USING LUMINESCENCE

This invention relates to methods of preparing and analysing particulate matter of biological origin by luminescence detection.

There are many fluids both biological and non-biological which contain substances which may require analysis either using a luminometer or other luminescence detection methods. The fluids may be biological e.g. blood, blood components, milk, colostrum, urine, tissue and tumour disaggregates and exudates, lymph, ascites fluid, cerebrospinal fluid, bile and other secretions and excretions of living organisms or non-biological e.g. fresh water (rivers, lakes, ponds), sea water, industrial effluent, leachates. The substances may be particulates of cellular or non-cellular varieties such as leucocytes, platelets, components from tissue disaggregates, components from tumours, protozoa, small invertebrates, algae including blue greens, gametes and generally any other particulate material of a biological origin which can be separated from its carrier fluid.

Much information can be obtained for example from measuring light emission from particles such as leucocytes. This light emission can be enhanced by adding luminogenic materials such as Pholasin (TM) and light can be measured in various ways. Pholasin reacts with oxygen radicals and other oxidants to produce light and leucocytes and other cells produce oxygen radicals when activated. There is a rapidly growing interest in the involvement of oxygen radicals in oncology, cardiology, rheumatology, asthma, ageing, autoimmune diseases and diabetes mellitus for example. In addition, there are the potentially damaging effects of cells activated during renal dialysis or reperfusion of organs during surgery. Other areas include study and assessment of disease activity in inflammatory diseases and for distinguishing between inflammation and infection, these areas being of particular interest to rheumatologists and haemotologists. A quantitative measure of particulate activity, for example the activity of leucocytes, would therefore be a valuable diagnostic tool.

In order to obtain quantitative results that can be used in diagnostic and comparative studies, it is essential that: a constant proportion of certain particles (preferably 100%) is removed from a fixed volume of fluid which might contain a mixture of particles; that the particles are not damaged in the process; that whatever treatment the particles experience during any manipulation can be repeated in an identical fashion on particles from another sample of fluid; that all parameters can be controlled so that the results can be compared and related to known factors.

There are known methods for separating particles, such as leucocytes, from blood, for example, for subsequent use in analysis. Such methods include multistep procedures including sedimentation with dextran, followed by separation on density gradients. These procedures involve centrifugation, mixing, incubating and sometimes lysis of unwanted red blood cells. They take a number of hours to complete, involve skilled operatives and subject the cells to uncontrollable variables which may inadvertently affect their subsequent response to analytical procedures (Boyum, A. (1968) Isolation of mononuclear cells and granulocytes from human blood. Scand. J. Clin. Lab. Invest. 21, Supple 97 (paper IV), 77–89). In addition the process has to be conducted in a laboratory and thus cannot be used in general medical or veterinary practice, at the bedside, in the field or in an outpatient clinic for example.

In response to the need for a rapid, simple and reliable method of isolating leucocytes from whole blood a simpler method was introduced (Ferrante, A. and Thong, Y. H. (1980) Optimal conditions for simultaneous purification of mononuclear and polymorphonuclear leucocytes from human peripheral blood by the HypaqueFicoll method. J Immunol Methods. 35, 109117), which involved layering whole blood on to a mixture of Ficoll and sodium and/or meglumine diatrizoate prepared to specific densities, centrifuging the tube and collecting layers of leucocytes which were washed with centrifugation 2 to 3 more times. This 'improved' method which, enabled leucocytes to be separated, washed and ready for analysis in about 1 to 2 hours still required a skilled operative and the need for a centrifuge. Also, it was not possible to carry out the procedure simultaneously on more than a very few samples (less than 4) and the method is not suitable for most bloods other than human, does not work efficiently on blood from people with, for example: juvenile rheumatoid arthritis, microcytic hypochromic anaemia. The method may fail or give variable results if an individual was receiving aspirin, indomethacin, prednisone or aurothioglucose, or other drugs in the treatment of bronchial congestion, immunodeficiency anaemia and other diseases. An improved method, designed to enable leucocytes to be separated from these 'difficult' bloods was developed (Ferrante, A., James, D. W., Betts, W. H. and Cleland, L. G. (1982) Rapid singlestep method for purification of polymorphonuclear leucocytes from blood of patients with rheumatoid arthritis. Clin exp. Immunol 47 749752) in which the viscosity of the density medium was changed. The results of this improved method are still variable and not useful for quantifiable and comparative results. In all the methods, even the improved ones, the cells are subjected at times to adverse conditions. And while it might be theoretically possible for a trained operative to work in precisely the same manner at each separation, the differences in the blood make it impossible for the blood from different people and at different states of a disease to behave in precisely the same manner. And it is impracticable, even for trained operatives, to standardise the ways they perform the various manipulations involved in the procedure. The method is therefore only suited to the separation of leucocytes from whole normal blood.

Pall Corporation in U.S. Pat. No. 4,925,572 and U.S. Pat. No. 4,880,548, disclose filters for depleting the leucocyte concentration of whole blood and for reducing the concentration of leucocytes from platelet concentrates. These filters are used on-line during blood or platelet transfusions, whereby the filtrate which contains the red blood cells or the platelets is allowed to enter the circulation of the patient while the leucocytes are retained by the membrane.

According to a first aspect of the present invention there is provided a method of analysing particulate matter of biological origin comprising the steps of passing a fluid containing said particulate matter through a membrane which membrane is adapted to hold said particulate matter and subjecting said membrane together with said held particulate matter to analysis by luminescence detection.

Preferably said analysis involves a luminometer and said membrane may be placed in a luminometer cuvette or a microtitre plate prior to insertion into the luminometer.

In the method leucocytes and/or platelets from a known volume of whole blood are separated simply and rapidly from the rest of the blood components on to a filter support from which useful, quantitative and comparative measurements of light emission can be made. The measurement of light, or other parameters, can be made a very short time, preferably within two minutes, after collection of blood. The procedure can be performed on blood from people excluded from the methods described above and also from blood from nonhuman species, which also do not separate properly using the above improved methods. The fluid from which the leucocytes are separated can in addition to blood be milk, urine, cerebrospinal fluid and any other fluid in which such particles are found. The method can also be applied to the separation of particles other than leucocytes and any substances that adheres to the membrane and can be analysed.

In a preferred method there is included the step of treating the particulate matter held by the membrane with a luminescent material which reacts with certain chemicals in or produced by the particulate matter. It is also possible that more than one luminescent material is used and these luminescent materials may be applied before or after the membrane is inserted in the luminometer.

In preferred methods said certain chemicals are radicals, such as superoxide, $O_2$ and the luminescent materials may be chosen from the from the following examples, PHOLASIN, luminol, lucigenin. Other chemicals such as ATP react with firefly luciferin plus firefly luciferase whereas bacterial luciferase is the preferred luminogenic reagent when analysing for NADPH and NADH.

Conveniently, the particulate matter held by the membrane is washed prior to being treated with said one or more luminescent materials. Examples of the washing substances are buffered or unbuffered salt solutions, blood serum, plasma. In a further embodiment the fluid passes through other membranes, each of which is adapted to prevent the through flow of other preselected substances.

Preferably the fluid passed through the filter by gravity or increased pressure on the fluid or reduced pressure on the downstream side or a combination of these, or by the capillary attraction of an absorptive pad held against the underside of the filter.

According to a second aspect of the present invention there is provided a filter device for filtering a fluid containing particulate matter of biological origin, said device containing a membrane through which, in use, the fluid is passed to leave the particulate matter, the membrane being adapted for use in luminescence detection apparatus to enable the particulate matter to be analysed.

Preferably the membrane is removable from the device for use with the luminescence detection apparatus.

In a preferred embodiment the membrane is adapted to remove said particulate matter by adsorption and has a Critical Wetting Surface Tension greater than 53 dynes/cm.

Another arrangement has the membrane held between two separable parts. Conveniently the membrane sits on a perforated support and may have its edges sealed or clamped between upper and lower frames.

Clearly the device may have more than one membrane for removing different substances from the fluid.

According to a third aspect of the present invention there is provided a syringe comprising a barrel having a fluid inlet, a plunger slidably disposed in the barrel and means for piercing the plunger whereby, in use, after filling the plunger can be pierced to allow the liquid in the syringe to be exposed to the atmosphere at the plunger as well as at the fluid inlet and thus to allow liquid to flow from the syringe without moving the plunger axially relative to the barrel.

Preferably the plunger has a rod connected to it by which the plunger is moved and the piercing means comprises a pin slidably mounted coaxially within said rod. Also the rod may have a screw thread at its distal end engaging in a matching screw thread in the plunger. Rotation of the rod allows the controlled exposure of the contents of the syringe to the atmosphere at the plunger end.

Embodiments of the invention will now be described in more detail. The description makes reference to the accompanying drawings in which:

FIG. 1(a) is a sectional view of a filter arrangement according to an aspect of the present invention.

FIG. 1(b) is a sectional view of an alternative part of the filter arrangement shown in FIG. 1(a).

Figure 3C:
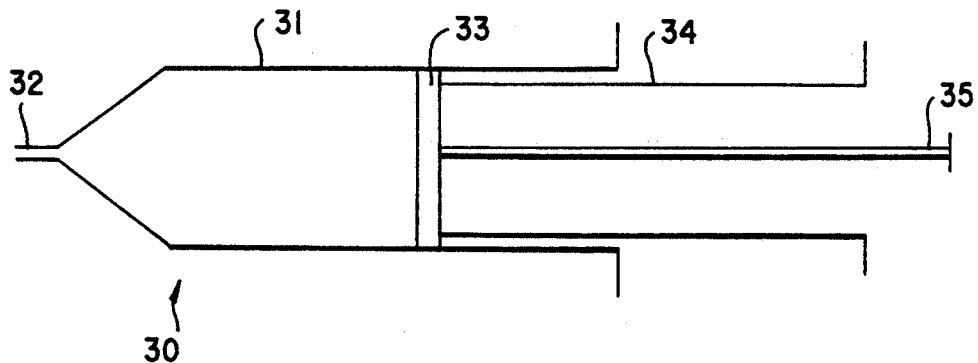
Figure 4:
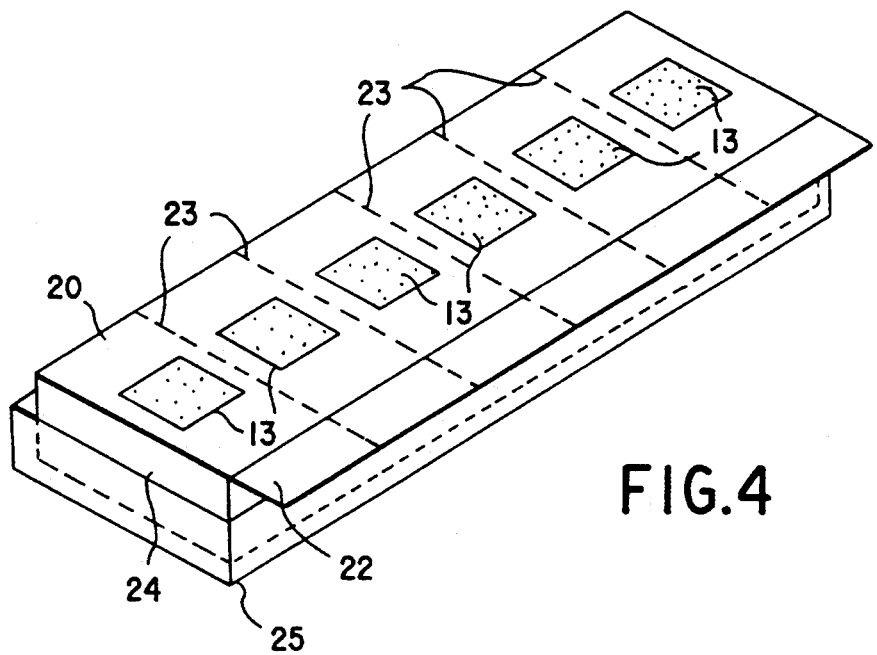
Figure 5:
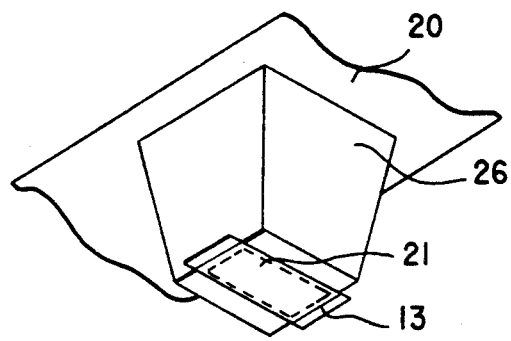

FIGS. 2(a) to (c) show various types of membrane for use in the filter arrangements, FIGS. 3(a) to (c) are diagrammatic section views of a syringe according to other aspects of the present invention, FIG. 4 is a perspective view from above of a further filter arrangement according to the present invention, and FIG. 5 is a perspective view from below of part of a still further filter arrangement according to the present invention.

It is often necessary to remove substances, such as cellular and/or non-cellular particulates or other dissolved substances, from a carrier fluid which may be biological or non-biological, so that the substance can be analysed. The fluids are collected in a number of ways which could range from a syringe to a beaker.

The fluid is then passed through a filter arrangement 10 as shown. In FIG. 1(a) the filter arrangement 10 comprises a funnel 11 having a perforated support 12 on which sits a membrane 13 the latter having a greater diameter than that of the perforated plate. A tubular reservoir 14 is attached to the funnel for gravity filtration of the fluid and the size of the membrane 13 is such that it is held in position by the reservoir 14 when the reservoir is screwed into place. In FIG. 1(b) there is shown an alternative reservoir provided with a Luer fitting 15. As will be readily appreciated the fluid is able to pass through the membrane either under gravity or by applying an increased pressure to the liquid or by reducing the pressure on the downstream side of the membrane. Clearly it is also possible to use a combination of these techniques as is well known.

More than one membrane could be employed, the purpose of such a technique being to collect different substances on different membranes. The construction of such a modification is not described because it clearly involves putting the membranes downstream from one another. Similarly each membrane can be made up of a number of layers of suitable materials.

The membranes themselves will not be discussed in detail. Membranes or other filters are well known to remove certain substances so as to purify the fluid which passes through the filter unhindered. however, Pall Corporation have invented certain membranes for using in obtaining blood and platelet concentrate which is free of leucocytes which are retained on the filter membrane by adsorption. However, bacteria and other substances are retained by careful regulation of the pore sizes in the membrane, less than 0.2 um in the case of bacteria.

With the FIG. 1 arrangements in which the membrane 13 is removable, the membrane will ideally be supplied in the form of individual units of the correct shape. This may be circular, rectangular or any other suitable shape. If a number of layers of filter material are used for each membrane then they may be left loose at the edges (FIG. 2(a)) or they may be sealed in some suitable way for example by melting, by using a filler 18 FIG. 2(b) or by clamping the edges between two frames 19 (FIG. 2(c)).

Once the fluid has been filtered, the substance may be washed so as to remove any part of the fluid which could interfere with subsequent use of the membrane. Such washing fluids may include buffered or unbuffered salt solutions or biological fluids such as blood serum or plasma.

One particular type of analysis which is of interest is luminometry although it will be realised that many other methods of analysis are envisaged.

Where the membrane is removable from the filter arrangement the membrane is then placed in a luminometer cuvette or microtitre plate or any other suitable receptable from which light can be detected. When inserted into the luminometer the upstream side of the membrane should face the light detector in the luminometer. If using a microtitre plate, the membrane should conform to the shape of the wells in the plate.

When measuring light emitted from the substance retained by the membrane, the membrane is treated or immersed in a base liquid which includes one or more luminescent materials such as PHOLASIN (Trade Mark), luminol, lucigenin, firely luciferase plus firely luciferin, and bacterial luciferase for example. The principles of analysis by luminescence are well known. Luminescent materials emit light in response to certain chemicals. One such chemical which stimulates PHOLASIN is superoxide, $O_2^-$ radical. Obviously the luminescent material chosen depends on the features which you wish to detect and analyse. More than one luminescent material can be present in the base liquid if desired so as to monitor different chemicals.

Various measurements can then be taken on the luminometer such as the resting glow of the luminescent material, the glow caused by metabolites of the substance under analysis, the resting glow of other luminescent materials together with any glow caused by metabolites.

Also, other substances could be introduced to the membrane whilst in the luminometer so as to activate certain other chemicals which could result in a different glow for measurement. For example, leucocytes are activated by a number of substances such as phorbol myristate acetate, tumor necrosis factor, opsonised serum, opsonised zymosan, a suspension of latex particles. The luminometer can be used to monitor the progress of the reactions.

The measurements made can give diagnostic indications of the physiological or pathological state of a patient. The membranes and the substances retained thereon are ready for analysis within minutes of the collection of the fluid. The process can readily be conducted in situ and therefore removes the expensive and time consuming step of sending the fluid to a specialised laboratory.

The apparatus could be supplied in kit form comprising say a syringe to obtain the fluid, a filter arrangement to isolate the substance of interest on the membrane and luminescent material to enable the membrane to be treated after insertion into a luminometer, portable luminometers being readily available. Clearly however suitable adaptions will be necessary to enable the kit to be used with all commercially available luminometers.

A further filter arrangement is shown in FIG. 4 and comprises a piece of membrane 13 which is attached (removably or immovably) to a support. The support may be in the form of a rigid strip 20 with rectangular holes cut in it at intervals and below which is attached the membrane. Other hole shapes are of course possible.

The support 20 may have an extension in the form of a flange 22 adapted to be held by forceps. The flange can be removed by cutting when the strip has been placed in the luminometer cuvette, thus obviating the need for the strip to be handled in any way.

At the end of the filtration, and subsequent washing of the membrane 13, i) if the membrane were removably attached to its support, the membrane would be removed from its support, perhaps by peeling, and placed in the luminometer cuvette; ii) if the membrane were immovably attached to its support, the support would be cut along guide lines 23 in such a way as to free a section of it containing the membrane from the rest of the support and this section would be placed in the luminometer cuvette.

A relatively thick absorptive pad 24 is held under the filter assembly so that fluid added to the membrane would pass through the membrane, after leaving the desired components in or on the membrane, and be absorbed by capillary attraction into the absorptive pad 24.

The absorptive pad 24 would itself be contained in a structure or enclosure 25 that would allow none of the absorbed fluid to spill from the sides or bottom of the pad other than into this enclosure 25. Alternatively this structure could form an integral part of the absorptive pad, such that the pad 24 is formed with impermeable side and bottom walls.

In another arrangement (not shown) the membrane, or sections of the membrane, may be held between two layers of supporting material in which are formed opposed holes for the passage of the fluid through the membrane and into the absorptive pad. In this case the appropriate piece of membrane would be removed from between the sandwich after filtration and washing and placed in the luminometer cuvette.

In another possible arrangement shown in FIG. 5 the support 20 may be in the form of a strip 20 containing a number of wells 26, perhaps six. FIG. 5 is of such a structure and shows one well viewed from underneath, this figure is to no particular scale. Each well has a hole 21, perhaps rectangular, at the bottom, below which the membrane 13 is attached.

If the luminometry is to be carried out in a micotitre plate luminometer the filtration device may consist of a microtitre plate strip or block in which the base of each well is furnished with a piece of the membrane as in the other devices described above. After filtration and washing of the samples, the strip or block is placed into a similar but shorter strip or block with the bottoms of the wells entire so that further flow of fluid through the membrane is prevented. This compound structure is then placed in the microtitre plate reader, perhaps after the addition of appropriate reagents to each of the wells.

The techniques described can also be used to test milk for various reasons. One reason is to analyse the leucocytes which are present in milk to gain information about certain diseases in the animals, for example mastitis in cows. Milk producers can claim a premium if their product reaches certain standards. Data can therefore be obtained almost instantaneously in situ, without the need for skilled labor. Such techniques will also have obvious benefits in third world countries where alternative facilities for testing may not be available.

Also milk can be tested in this way to assess under—or over—pasteurisation by for example analysing the concentration of various enzymes. Bacterial contamination could also be monitored at the same time.

Another application for this invention is for the rapid determination of leucocytes in urine as part of a luminescent urinary tract infection screening kit. The activity of any leucocytes present in the urine and adsorbed on to the membrane will be assessed with the luminogenic reagent Pholasin or other suitable reagents. The invention will provide a simple, rapid measure of pyuria and its relation to bacteriuria. It will lead to simplification of the luminescent test for determining bacteria in urine, eliminating the requirement to destroy any ATP from somatic cells which might be present. Elimination of such a step will increase both the speed and reliability of that test.

FIG. 3(a) shows a syringe 30 having a barrel 31 and an inlet 32 through which liquid is drawn when a plunger 33 is withdrawn. The plunger 33 being pulled back by rod 34 attached thereto. A pin 35 is disposed within the rod 34 so that when the syringe 30 has been filled, the plunger can be pierced. The fluid in the syringe can then flow out under gravity. This is advantageous because it is not always desirable to eject the fluid under pressure by depressing the plunger. Clearly other ways of exposing the fluid at the plunger end to atmospheric pressure, for example the rod 34 may be attached to the plunger 33 by means of a screw thread passing through the plunger as shown in FIG. 3(b) by means of a bayonet fitting plunger are possible and need not be confined within the rod 34.

FIG. 3(c) shows another syringe 30 in which the rod 34 is in the form of a cylinder which surrounds the pin 35. In use, when the syringe is held vertically so that the contents can be allowed to flow out at a rate controlled by the pin 35, another fluid is introduced into the cylinder 34. If the second fluid is of lower density than the contents of the syringe it will flow into the barrel and flush out the barrel of the syringe. When this second liquid impinges on the filter it will act as a washing liquid to wash away any substances not intended to be retained by the filter material. A similar adaptation could be made to the other syringe embodiments mentioned.

We claim:

1. A method of analyzing the leucocytes in a leucocyte-containing biological fluid comprising the steps of:
   (i) passing said biological fluid through a filter material having a critical wetting surface tension greater than 53 dynes/cm and capable of holding said leucocytes by adsorption;
   (ii) treating said filter material together with said held leucocytes with one or more luminogenic materials; and
   (iii) subjecting said treated filter material with said held leucocytes to analysis by luminescence detection.

2. A method as claimed in claim 1, wherein said filter material with said held leucocytes is introduced into a luminometer.

3. A method as claimed in claim 2, wherein said filter material with said held leucocytes is placed in a luminometer cuvette or on a microtitre plate prior to insertion into the luminometer.

4. A method as claimed in claim 3, wherein the leucocytes held by the filter material are washed before being treated with the one or more luminogenic materials.

5. A method as claimed in claim 1, further comprising the step of drawing the fluid through the filter material by use of an absorptive pad disposed below the filter material.

6. A filter device for filtering a leucocyte-containing biological fluid, said device containing a filter material through which, in use, the fluid is passed to leave the particulate matter on the filter material, the filter material being attached to a support means, said support means comprising a plate having at least one hole below which the filter material extends thereby to constitute one or more filtering stations and the filter material having a critical wetting surface tension greater than 53 dynes/cm and capable of holding said leucocytes by adsorption wherein the filter material is removable from the device prior to use in a luminescence detection apparatus to enable the particulate matter held on the filter material to be analyzed.

7. A filter device as claimed in claim 6, wherein the filter material is removable from the plate prior to insertion in the luminescence detection apparatus.

8. A filter device as claimed in claim 6, wherein the plate is formed with at least one well, said at least one hole being formed in the base of said at least one well.

9. A filter device as claimed in claim 6, wherein an absorptive pad is disposed below the filter material to draw the fluid through the filter material.

* * * * *